US00PP17137P3

(12) United States Plant Patent
Gerawan

(10) Patent No.: US PP17,137 P3
(45) Date of Patent: Oct. 10, 2006

(54) 'GP-27' PEACH

(50) Latin Name: *Prunus persica*
Varietal Denomination: GP-27

(75) Inventor: Michael R. Gerawan, Reedley, CA (US)

(73) Assignee: Gerawan Farming, Sanger, CA (US)

( * ) Notice: Subject to any disclaimer, the term of this patent is extended or adjusted under 35 U.S.C. 154(b) by 185 days.

(21) Appl. No.: 10/888,114

(22) Filed: Jul. 9, 2004

(65) Prior Publication Data

US 2006/0010539 P1 Jan. 12, 2006

(51) Int. Cl.
*A01H 5/00* (2006.01)

(52) U.S. Cl. ..... Plt./198

(58) Field of Classification Search ..... Plt./198
See application file for complete search history.

(56) References Cited

U.S. PATENT DOCUMENTS

PP9,438 P * 1/1996 Doyle ..... Plt./198
PP12,405 P2 * 2/2002 Slaughter et al. ..... Plt./198

* cited by examiner

*Primary Examiner*—Kent Bell
*Assistant Examiner*—W. C. Haas
(74) *Attorney, Agent, or Firm*—Townsend and Townsend and Crew LLP

(57) ABSTRACT

A new and distinct variety of peach *Prunus persica*, tree substantially as illustrated and described which produces large and attractive fruit which are mature for commercial harvesting and shipment approximately August 23 to September 8, nearly 2 weeks before 'Prima Gattie' peach tree (U.S. Plant Pat. No. 10,085), in the San Joaquin Valley of central California.

1 Drawing Sheet

Botanical designation: *Prunus persica.*
Variety denomination: 'GP-27'.

BACKGROUND OF THE INVENTION

The present invention relates to a new and distinct variety of peach tree, which will hereinafter be denominated varietally as 'GP-27' peach tree, and, more particularly, to a peach tree which produces fruit, which are mature for commercial harvesting and shipment approximately August 23 to September 8 in the San Joaquin Valley of central California.

Commercially acceptable fruit is abundant in the case of many varieties of fruit trees. This is particularly true of peach trees. The plentiful quantities of such commercially acceptable fruit result in there being a substantial market for such fruit throughout most of a comparatively long growing season.

However, commercially acceptable fruit is relatively rare at the initiation and termination of the growing season. Most such early or late ripening peach varieties produce fruit which is only marginally acceptable on a commercial basis in that it is small in size, or possesses poor skin coloration, or lacks desirable flavor, or has poor handling characteristics, or any combination of these and other negative characteristics. Accordingly, new peach varieties producing fruit which ripens early or late in the season, but which possesses characteristics more typical of fruit ripening more nearly at the height of the growing season are of significant commerical value. The new variety of peach tree of the present invention appears to be such a variety, as will hereinafter be set forth in greater detail.

BRIEF SUMMARY OF THE INVENTION

The 'GP-27' peach tree is characterized by producing a large, high quality, freestone fruit which have superior external coloration and are ripe for commercial harvesting and shipment approximately August 23 to September 8 in the San Joaquin Valley of central California. The new variety is most closely similar to the 'Autumn Flame' (U.S. Plant Pat. No. 9,438) peach tree, which produces fruit ripening at nearly 2 weeks later in the growing season. However, the fruit of the instant variety is distinguishable from the fruit of the 'Autumn Flame' peach tree in that the new variety produces heavy crop on consistent basis. The flavor of the new variety is substantially improved over that of the 'Autumn Flame' peach tree, remaining sweet and pleasant even in heavy crop production. In addition, the coloration of the fruit of the new variety is greatly improved over that of the 'Autumn Flame' peach tree, developing from thirty percent (30%) to eighty percent (80%) red blush in both a washed and striped to dappled pattern, while in the case of the fruit of the 'Autumn Flame' peach tree, the red blush coloration extends only over from ten percent (10%) to forty percent (40%) of the fruit surface under normal growing conditions.

BRIEF DESCRIPTION OF THE DRAWINGS

The accompanying drawing is a color photograph showing mature fruit of the new variety including a first in top plan view showing the base thereof; a second in side elevation showing the suture thereof; a third in bottom plan view showing the apex thereof; a fourth sectioned and laid open to show the flesh and the stone cavity thereof; a fifth in side elevation; and a stone and foliage typical of the new variety of peach tree.

DETAILED DESCRIPTION OF THE INVENTION

The variety was discovered as a seedling by the inventor in September, 1994 near Sanger in the San Joaquin Valley of central California. The new variety was asexually reproduced by grafting wood of the new variety on Nemaguard peach rootstock. The new variety was asexually reproduced in February, 1997 under the direction of the inventor near Sanger in the San Joaquin Valley of central California. The inventor has continued to observe the asexually reproduced peach trees of the new variety and has confirmed that they are identical in all respects to the parent.

Referring more specifically to the pomological details of the new and distinct variety of peach tree, the following has been observed in the microclimatic ecological conditions prevailing at the orchard of origin located in Eastern Fresno County near the town of Sanger. All major color codes designations are by reference to The R.H.S. Colour Chart (1995 Third Edition) provided by The Royal Horticultural Society of Great Britain.

Tree:

*Generally*.—Eventual tree form and density are determined by the training system used in the orchard. The subject orchard has been trained using the standard "open vase" system. The test orchard was propagated in 1997 on 'Nemagard' rootstock, and is in sixth leaf.

*Size*.—Variable. Ranges from 304.8 cm (10 feet) to 365.7 cm (12 feet) in height and from 335.28 cm (11 feet) to 396.24 cm (13 feet) in width.

*Vigor*.—Moderately vigorous and hardy.

*Figure*.—Upright to upright-moderately spreading in form.

*Productivity*.—Productive, 413 pounds per tree.

*Regularity of bearing*.—Regular under typical central San Joaquin Valley climatic conditions.

Trunk:

*Size*.—Average in thickness from 13.4 cm (5.28 inches) to 18.7 cm (7.36 inches) in diameter.

*Surface texture*.—Rough in bark texture. The bark surface is moderately scaly with a moderate amount of scarfskin present.

*Color*.—RHS Grayed-Orange Group 165 A, FAN 4.

*Lenticels*.—Numerous bark lenticels are present, 6 to 8 per square inch on the trunk and 1 per square inch on branches. They are small to medium in size and oval to slightly oblongish in form. Length — 3 mm (0.118 inches) to 9.0 mm (0.354 inches). Height — 1 mm (0.039 inches) to 2.0 mm (0.079 inches).

Branches:

*Size*.—Average in thickness, similar in thickness to those found on the O'Henry peach tree.

*Surface texture*.—Moderately rough.

*Color*.—Two year or older wood — Medium brown, RHS Greyed-Orange Group N 167 B to C, FAN 4. Color — immature branches — Pale green, RHS Greyed-Green Group 195 B, FAN 4. Color of the new shoot tip is a bright green-yellow, RHS Yellow-Green Group N 144 D, FAN 3.

*Internode*.—Length — On bearing branches, ranges from 18 mm (0.709 inches) to 29 mm (1.141 inches) between nodes as measured at mid-stem on current season's growth.

Leaves:

Size:

*Generally*.—Medium to large. Leaf measurements are from large leaves growing near midpoint of actively growing upright current season's shoots.

*Average length*.—17.5 cm (6.89 inches) to 21.5 cm (8.464 inches) including the leaf petiole.

*Average width*.—4.2 cm (1.653 inches) to 5 cm (1.97 inches).

*Leaf thickness*.—Normal.

*Form*.—Lanceolate with acuminate tip. Leaf apices often are slightly twisted sideways and abruptly bend downwards.

Color:

*Upwardly disposed surface*.—RHS Green Group 139 A, FAN 3.

*Downwardly disposed surface*.—RHS Green Group 138 A to B.

Marginal form:

*Generally*.—Crenate, with broad, low, regular crenations.

*Leaf margin*.—Moderately undulate.

*Glandular characteristics*.—Glands are small to medium in size. Gland form is generally reniform. On the leaf blade gland number is variable, from 1 to 4 present on the base of the leaf blade. Glands present on the blade are always reniform. From 1 to 3 additional reniform glands are present on the petiole or right at the petiolar junction with the basal leaf margin. The glands are alternate in position.

*Leaf gland color*.—Bright shiny green-yellow when young, RHS Yellow-Green Group 145 C, FAN 3, becoming dark and deteriorating with age.

Petiole:

*Size*.—Relatively medium.

*Length*.—8 mm (0.315 inches) to 12 mm (0.472 inches).

*Thickness*.—2.0 mm (0.079 inches).

*Color*.—Pale green, RHS Yellow-Green Group 147 C, FAN 3, with a darker green coloration within the petiole groove, RHS Yellow-Green Group 146 B, FAN 3.

*Stipules*.—Moderately long. The stipules are present primarily on every new shoot growth and are early deciduous.

*Length*.—7 mm (0.276 inches) to 12 mm (0.472 inches).

*Form*.—Linear lanceolate with serrate margins.

*Color*.—Bright green-yellow, RHS Yellow-Green Group 146 D, FAN 3, becoming darker with age and rapidly deteriorating.

Flowers:

*Flower buds*.—Dormant flower buds are medium in size and conic in form. Bud scale coloration is RHS Grey Group 201 D, FAN 4. The buds are free from the bearing stem. The bud scale surfaces are very finely pubescent with a dense gray colored pubescence. The buds are hardy under typical central San Joaquin Valley climatic conditions.

*Date of bloom*.—The bloom of the new variety is slightly late in relation other commercial peach cultivars commonly grown in the central San Joaquin Valley region. Date of first bloom was Feb. 26 in 2002, and date of full bloom was Mar. 6 in 2002.

*Bloom quantity*.—Abundant. Flower number per node varies from 1 to 3, but mostly 2 on fruitful hanger shoots.

Size:

*Generally*.—Large showy flower. Flower diameter fully expanded ranges from 40 mm (1.575 inches) to 50 mm (1.969 inches). The flower remains slightly cupped inward even when fully mature.

Petals:
*Size*.—Medium to large.
*Length*.—20 mm (0.787 inches) to 25 mm (0.984 inches).
*Width*.—16 mm (0.630 inches) to 22 mm (0.866 inches).
*Form*.—Variable but most frequently oval with petal margins slightly rolled upwards.
*Number*.—Five.
*Color*.—Young petals are light pink (RHS Red Purple Group 69 B to C, FAN 2) on the petal interior, and a darker pink (RHS Red- Purple Group 67 B, FAN 2) at the petal claw.
*Claw form*.—Narrow and truncate in form.
*Margins*.—Slightly undulate.
*Apex*.—The petal apices are variable in form, but are generally rounded and usually very slightly undulate.

Flower pedicel:
*Size*.—Small medium, ranging from 1 mm (0.039 inches) to 2 mm (0.079 inches) in length.
*Thickness*.—1.0 mm (0.039 inches).
*Color*.—Bright shiny green (RHS Yellow-Green Group 145 A to C, FAN 3).
*Surface*.—Glabrous.

Nectaries:
*Color*.—Young nectaries are bright orange (RHS Orange Group N 25 A, FAN 1), darkening and becoming somewhat dull with age.

Anthers:
*Size*.—Medium.
*Color*.—Freshly opened flowers RHS Red Group 39 A to B, FAN 1, both ventrally and dorsally.
*Pollen*.—Abundant.

Pollen:
*Color*.—RHS Yellow-Orange Group 18 B to C, FAN 1.

Stamens:
*Numbers*.—Variable 33 to 45, but mostly in mid forties.
*Length*.—Moderately long ranging from 9 mm (0.354 inches) to 15 mm (0.787 inches). Stamen length is variable in relation to the pistil, mostly longer, 3 to 6 shorter, at other times shorter or about equal.

Filament:
*Color*.—When young RHS Purple Group 75 D, FAN 2, turning to RHS Red-Purple Group 68 A to B, FAN 2, with maturity.

Pistil:
*Length*.—Variable, ranging from 15 mm (0.590 inches) to 18 mm (0.709 inches), including the stigma, style and ovary.
*Ovary color*.—RHS Green Group 138 D, FAN 3.
*Surface*.—Highly pubescent.

Sepals:
*Number*.—Mostly 5.
*Sepal apices*.—Rounded.
*Sepal color*.—RHS Red-Purple Group 61 A, FAN2.
*Sepal greenish margins color*.—RHS Green Group 130 D, FAN 3.
*Sepal length*.—Generally 5 mm (0.197 inches) to 8 mm (0.315 inches).
*Sepal width*.—Generally 4 mm (0.157 inches) to 5 mm (1.197 inches).
*Sepal margins*.—Entire.

Fruit:
Maturity when described: Firm ripe condition typical of full commercial maturity. In 2002, the first pick was on August 23, approximately 8 to 10 days before the 'Prima Gattie' (U.S. Plant Pat. No. 10,085), and the last pick was on September 8 near Sanger, under the prevailing ecological conditions of the San Joaquin Valley of Central California.

Size:
*Generally*.—Large and uniform.
*Average diameter in the check plane*.—73 mm (2.8762 inches) to 78 mm (3.0732 inches).
*Average diameter transverse in the suture plane*.—71 mm (2.7974 inches) to 78 mm (3.0732 inches).
*Average diameter in the axial plane*.—72 mm (2.8362 inches) to 78 mm (3.0732 inches).

Form:
*Symmetry*.—Usually asymmetrical with one fruit half very slightly larger than the other.
*Lateral*.—Variable, from ovate to nearly globular.
*Apical*. —Somewhat variable, usually globose, but at times with an elongated ventral suture area.

Suture:
*Generally*.—Relatively shallow, conspicuous to inconspicuous line extending from base to apex, with a slight depression before and after the pistil point, somewhat deeper within the stem cavity basin. The suture has no distinctive coloration of its own, but takes on the coloration of the underlying blush or ground color. The suture color ranges from RHS Yellow-Orange Group 14 C to Yellow-Orange Group 17 D, FAN 1.

Ventral surface:
*Generally*.—Slightly irregular and slightly rough, often with a slightly raised ventral surface, lipped on one side.

Stem cavity:
*Generally*.—Small to medium in size. The shoulders of the cavity are often creased with a groove where the fruit was attached to the bearing branch.
*Width*.—20 mm (0.7880 inches) to 27 mm (1.063 inches).
*Depth*.—15 mm (0.5910 inches) to 20 mm (0.7880 inches).
*Length*.—30 mm (1.1820 inches) to 40 mm (1.5760 inches).
*Shape*.—Oval.

Stem:
*Length*.—Varies from 11 mm (0.433 inches) to 14 mm (0.512 inches).
*Thickness*.—3.5 mm (0.118 inches) to 4.5 mm (0.138 inches).
*Color*.—RHS Yellow Green Group 144 D, FAN 3.
*Base*.—Shape is round to oblate.
*Form*.—Moderately oval.
*Angle*.—Slightly oblique to the fruit axis.

Apex:
*Shape*.—Generally rounded.
*Pistil point*.—Shape is very slightly pointed to the feel of finger tips.

Skin:
*Thickness*.—Average. Skin is tenacious to the flesh at commercial maturity.
*Texture*.—Surface is pubescent with a medium textured, short pubescence.
*Skin flavor*.—Relatively neutral.
*Tendency to crack and split*.—No tendency to crack or split has been observed.
*Color*.—Generally — Skin color is a somewhat uneven, but attractive, combination of red blush color and yellow ground color on tigery base. Blush color covers from twenty five percent (25%) to as much as seventy five percent (75%) of the fruit surface, with exterior and exposed fruit in the highest color ranges. Blush form varies from a washed pattern to light striping and dappled areas. Ground color covers from twenty five percent (25%) to seventy five percent (75%) of the fruit surface with the most interior fruit on the tree in the highest ground color ranges.

*Blush color*.—Intensity varies from a dark red RHS Red Group 46 A to RHS Orange-Red Group 33 A, FAN 1.

*Ground color*.—RHS Yellow-Orange Group 23 B to C, FAN 1.

*Skin base*.—Prominent tigery base all around except under dark red blush color.

Flesh:

*Flesh color*.—Somewhat variable. Generally, light yellow (RHS Yellow-Orange Group 18 A, FAN 1) from under the skin inward for 10 mm (0.394 inches) to 15 mm (0.591 inches). Numerous light colored fibers are present within the flesh.

*Color of stone cavity*.13 RHS Red-Purple Group 60 A, FAN 1 to RHS Red Group 45 A, FAN 1, with red streaks and flecking extending outward from the cavity 5 mm ( inches) to 25 mm (0.985 inches) into the flesh.

*Juice production*.—Becomes juicy with afterripening.

*Flavor*.—Sweet with moderate acidity and well balanced.

*Aroma*.—Slight and pleasant.

*Flesh texture*.—Very firm and fine textured.

*Ripening*.—Evenly throughout.

*Eating quality*.—Good.

*Brix*.—Generally ranges from 12 to 14.5.

Stone:

*Attachment*.—Freestone. The stone is only loosely held around the hilum at commercial maturity and rest is free to very loose from the flesh. The stone's surface, which is held around the hilum, is generally covered with short fibers and small pieces of adhering flesh.

*Fibers*. —Numbers — Some are attached to the held stone surface. Length — Short.

*Size*.—Generally — Medium. Length — 32 mm (1.2608 inches) to 39 mm (1.5366 inches). Width — 25 mm (0.985 inches) to 28 mm (1.1032 inches). Thickness — 18.0 mm (1.7092 inches) to 20.0 mm (0.788 inches).

*Form*.—Generally — Usually oval to semi-oval.

*Apex*.—Shape — Relatively variable, most frequently acute.

*Color*.—Fresh — Slightly stained near and around hilum where stone clings to flesh with a dark maroon coloration (RHS Red-Purple Group 60 A to B, FAN 2). Old dry — Dark brown (RHS Greyed-Orange Group 176 A to D, FAN 4).

*Base*.—Shape — Truncate. The base angle is usually oblique to the stone axis.

*Sides*.—Generally — Usually unequal.

*Surface*. —Moderately roughened laterally, substantially grooved over the apical shoulder area. Shallow grooves are present basally, converging basally.

*Ventral edge*.—Width — Medium. 3.0 mm (0.1182 inches) to 4.5 mm (0.1773 inches) at mid-suture.

*Wings*.—Several low coalesced wings are present, at times slightly more prominent basally.

*Dorsal edge*.—A shallow, often discontinuous groove is present basally, less distinct over the apical shoulder. The dorsal groove is bordered by two low ridges which are at times cross cut by several grooves. The apical shoulder is slightly eroded near the stone apex.

*Hilum*.—Medium to large in size, with a thick, substantially toughened and grooved collar.

*Hilum length*.—Generally 6.0 mm (0.2364 inches) to 9.0 mm (0.3546 inches).

*Hilum width*.—Generally 3.0 m (0.1182 inches) to 5.0 mm (0.197 inches).

*Hilum depth*.—Generally 0.5 mm (0.0197 inches) to 1.5 mm (0.0591 inches).

*Hilum color*.—RHS Greyed-Orange Group 173 D, FAN 4.

*Form*.—Oval.

Kernel:

*Kernel length*.—Generally ranges from 16.0 mm (0.6304 inches) to 20.0 mm (0.788 inches).

*Kernel width*.—Generally ranges from 12.0 mm (0.4728 inches) to 14.0 mm (0.5516 inches).

*Kernel thickness*.—Generally ranges from 4.0 mm (0.1576 inches) to 6.5 mm (0.2561 inches).

*Kernel shape*.—Oval to oblong, rounded base.

*Kernel apex*.—Moderately acute.

*Kernel color*.—Approximately RHS Greyed-Orange Group 165 C, FAN 4 to N 167 C, FAN 4.

*Tendency to split*.—No tendency to split has been observed.

*Use*.—Fresh market.

*Keeping quality*.—Excellent.

*Shipping and handling qualities*.—Excellent.

Although the new variety of peach tree possesses the described characteristics noted above as a result of the growing conditions prevailing near Sanger in the central part of the San Joaquin Valley of California, it is to be understood that variations of the usual magnitude and characteristics incident to changes in growing conditions, irrigation, fertilization, pruning, pest control, climatic variation and the like are to be expected.

What is claimed is:

1. A new and distinct variety of peach tree having the characteristics described and illustrated herein.

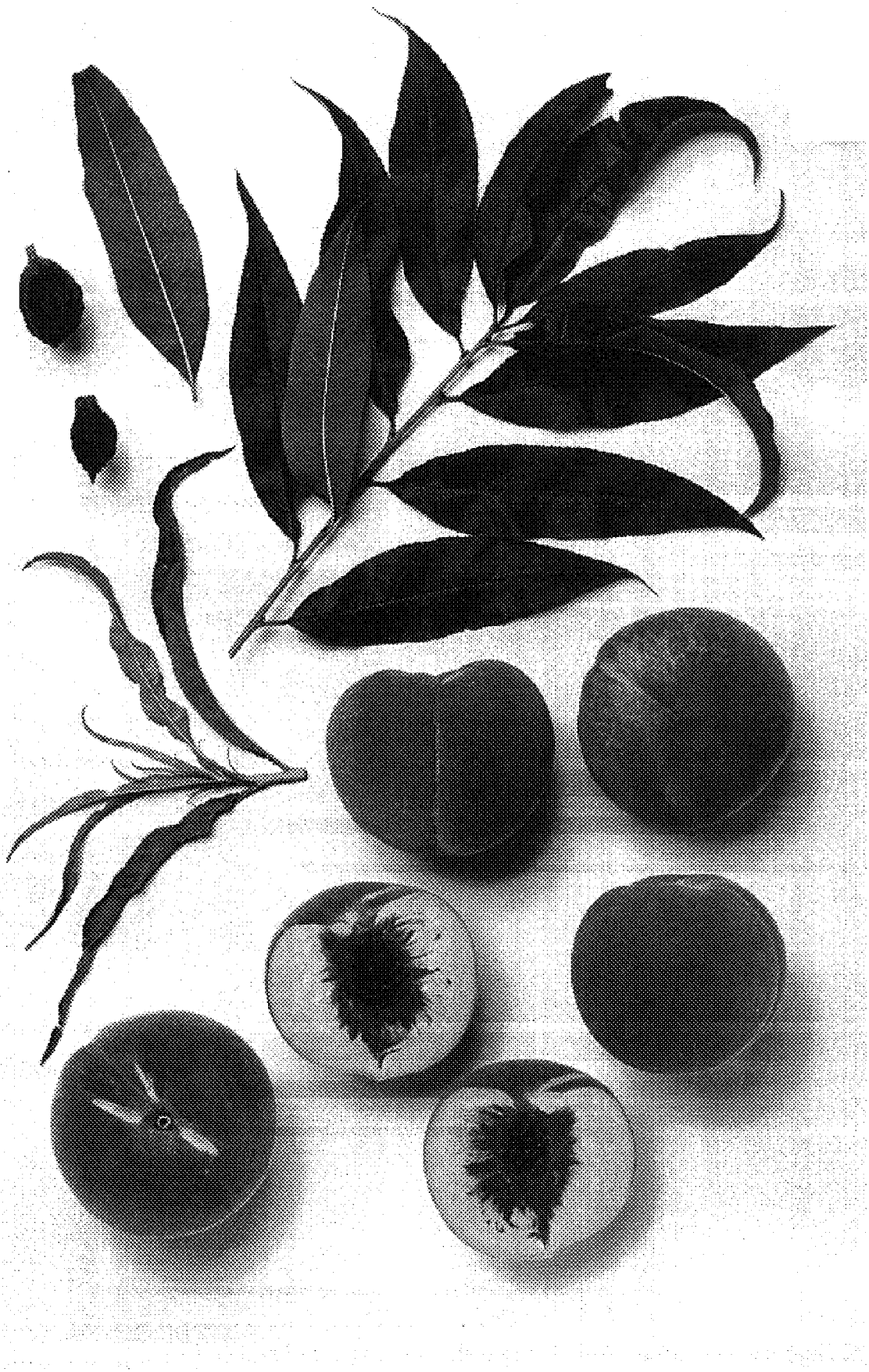

* * * * *